US012611216B2

(12) United States Patent
Baril et al.

(10) Patent No.: US 12,611,216 B2
(45) Date of Patent: Apr. 28, 2026

(54) PARTIAL CLIP CLOSURE MECHANISMS FOR SURGICAL CLIP APPLIERS AND SURGICAL CLIP APPLIERS INCORPORATING THE SAME

(71) Applicant: Covidien LP, Mansfield, MA (US)

(72) Inventors: Jacob C. Baril, Norwalk, CT (US); Garrett P. Ebersole, Hamden, CT (US); Saumya Banerjee, Southington, CT (US)

(73) Assignee: Covidien LP, Mansfield, MA (US)

( * ) Notice: Subject to any disclaimer, the term of this patent is extended or adjusted under 35 U.S.C. 154(b) by 354 days.

(21) Appl. No.: 17/896,391

(22) Filed: Aug. 26, 2022

(65) Prior Publication Data

US 2024/0065703 A1     Feb. 29, 2024

(51) Int. Cl.
*A61B 17/128* (2006.01)

(52) U.S. Cl.
CPC ............................... *A61B 17/1285* (2013.01)

(58) Field of Classification Search
CPC ... A61B 17/1285; A61B 34/37; A61B 17/122; A61B 17/1227; A61B 17/1222; A61B 17/29; A61B 18/1445; A61B 17/282
See application file for complete search history.

(56) References Cited

U.S. PATENT DOCUMENTS

| | | | |
|---|---|---|---|
| 6,099,537 A | | 8/2000 | Sugai et al. |
| 8,267,944 B2 | | 9/2012 | Sorrentino et al. |

| | | | |
|---|---|---|---|
| 8,512,357 B2 | | 8/2013 | Viola |
| 9,408,610 B2 | | 8/2016 | Hartoumbekis |
| 9,414,844 B2 | | 8/2016 | Zergiebel et al. |
| 9,468,440 B2 | | 10/2016 | Schulz et al. |
| 9,532,787 B2 | | 1/2017 | Zammataro |
| 9,968,362 B2 * | | 5/2018 | Malkowski ........ A61B 17/1285 |
| 11,998,216 B2 * | | 6/2024 | Harris .................... A61B 34/37 |
| 2005/0033278 A1 * | | 2/2005 | McClurken ............ A61B 18/14 |
| | | | 606/49 |
| 2005/0277959 A1 | | 12/2005 | Cosgrove et al. |
| 2007/0049947 A1 * | | 3/2007 | Menn ................... A61B 17/122 |
| | | | 606/142 |

(Continued)

OTHER PUBLICATIONS

Extended European Search Report dated Jan. 4, 2024, issued in corresponding EP Appln. No. 23193169, 7 pages.

*Primary Examiner* — Kathleen S Holwerda
*Assistant Examiner* — James S Mcginnity
(74) *Attorney, Agent, or Firm* — Dymera IP, LLC

(57) ABSTRACT

A surgical clip applier including an elongated portion, an end effector, and a partial clip closure mechanism is disclosed. The end effector includes a first jaw member defining a recess, and a second jaw member. At least one of the first jaw member or the second jaw member movable toward the other of the first jaw member or the second jaw member between an open position and a closed position. The end effector is configured to support a surgical clip between the first jaw member and the second jaw member. The partial clip closure mechanism includes a wedge that is selectively positionable in engagement with the recess. When the wedge is free from engagement with the recess, the jaw members are positionable in the closed position. When the wedge is in engagement with the recess, the jaw members are prevented from being positioned in the closed position.

20 Claims, 14 Drawing Sheets

(56)            References Cited

U.S. PATENT DOCUMENTS

| | | | |
|---|---|---|---|
| 2007/0191868 A1 | 8/2007 | Theroux et al. | |
| 2008/0033457 A1* | 2/2008 | Francischelli | A61B 17/1285 |
| | | | 606/157 |
| 2019/0059904 A1 | 2/2019 | Zammataro | |
| 2020/0046365 A1 | 2/2020 | Baril et al. | |
| 2020/0360023 A1* | 11/2020 | Bagley | A61B 17/128 |

* cited by examiner

100c

100b

550

PARTIAL CLIP CLOSURE MECHANISMS FOR SURGICAL CLIP APPLIERS AND SURGICAL CLIP APPLIERS INCORPORATING THE SAME

BACKGROUND

This disclosure relates to surgical instruments. More particularly, this disclosure relates to partial clip closure mechanisms for surgical clip appliers and surgical clip appliers including the same.

Surgical clip appliers are known in the art and are used for a number of distinct and useful surgical procedures including endoscopic, open, and robotic surgical procedures. Surgical clip appliers having various sizes (e.g., diameters) are configured to apply a variety of diverse surgical clips, and are capable of applying a single or multiple surgical clips within the body cavity. Such surgical clips are typically fabricated from a biocompatible material and are usually compressed over tissue. Once applied to tissue, the compressed surgical clip terminates the flow of fluid therethrough.

Certain surgical procedures or situations may benefit from the implementation of a partially-formed surgical clip to variably occlude a vessel, or to retain a catheter in a vessel without occluding the vessel (e.g., during cholangiograms), for instance.

SUMMARY

This disclosure relates to a surgical clip applier including an elongated portion, an end effector, and a partial clip closure mechanism. The elongated portion includes a distal end. The end effector is disposed adjacent the distal end of the elongated portion, and includes a first jaw member and a second jaw member. At least one of the first jaw member or the second jaw member is movable toward the other of the first jaw member or the second jaw member between an open position and a closed position. The first jaw member defines a recess. The end effector is configured to support a surgical clip between the first jaw member and the second jaw member. The partial clip closure mechanism includes a wedge that is selectively positionable in engagement with the recess of the first jaw member. When the wedge is free from engagement with the recess of the first jaw member, the first jaw member and the second jaw member are positionable in the closed position. When the wedge is in engagement with the recess of the first jaw member, the first jaw member and the second jaw member are prevented from being positioned in the closed position.

In disclosed embodiments, when the wedge is in engagement with the recess of the first jaw member, at least one of the first jaw member or the second jaw member is movable into a partially-closed position.

In disclosed embodiments, the second jaw member defines a recess. The wedge is selectively positionable in engagement with the recess of the second jaw member. In embodiments, the wedge is simultaneously positionable in engagement with the recess of the first jaw member and in engagement with the recess of the second jaw member.

In disclosed embodiments, the recess of the first jaw member defines a triangular shape.

In disclosed embodiments, the wedge includes a proximal portion forming a ramp to facilitate disengagement between the wedge and the recess of the first jaw member.

In disclosed embodiments, the wedge is biased into engagement with the recess of the first jaw member.

In disclosed embodiments, the first jaw member includes a rail, and the second jaw member includes a rail. The wedge is longitudinally translatable along the rail of the first jaw member and along the rail of the second jaw member.

In disclosed embodiments, the wedge includes a proximal portion and a distal portion. The proximal portion of the wedge is trapezoidal, and the distal portion of the wedge is triangular.

In disclosed embodiments, the partial clip closure mechanism includes a switch and an elongated link having a proximal portion and a distal portion. The switch is disposed in mechanical cooperation with the proximal portion of the elongated link, and the wedge is disposed adjacent the distal portion of the elongated link.

This disclosure also relates to a surgical clip applier including an elongated portion, an end effector, and a partial clip closure mechanism. The elongated portion defines a longitudinal axis and includes a distal end. The end effector is disposed adjacent the distal end of the elongated portion, and includes a first jaw member and a second jaw member. The first jaw member is movable toward the second jaw member between an open position and a closed position. The end effector is configured to support a surgical clip between the first jaw member and the second jaw member. The partial clip closure mechanism includes a wedge that is movable between a proximal position where the first jaw member is movable to the closed position relative to the second jaw member, and a distal position where the first jaw member is physically prevented from moving to the closed position relative to the second jaw member.

In disclosed embodiments, the wedge is movable in a direction that is parallel to the longitudinal axis. It is also disclosed that the wedge is movable in a direction that is disposed at an angle to the longitudinal axis.

In disclosed embodiments, the wedge includes a proximal portion forming a ramp to facilitate proximal movement of the wedge when the wedge is in the distal position.

In disclosed embodiments, the first jaw member includes a rail, and the second jaw member includes a rail. The wedge is longitudinally translatable along the rail of the first jaw member and along the rail of the second jaw member.

In disclosed embodiments, the wedge includes a proximal portion and a distal portion. The proximal portion of the wedge is trapezoidal, the distal portion of the wedge is triangular.

This disclosure also relates to a surgical clip applier including an elongated portion, an end effector, and a partial clip closure mechanism. The elongated portion includes a distal end. The end effector is disposed adjacent the distal end of the elongated portion, and includes a first jaw member having a recess, and a second jaw member having a recess. The end effector is configured to support a surgical clip between the first jaw member and the second jaw member. The partial clip closure mechanism includes a wedge that is movable between a first position where the end effector is permitted to fully form a surgical clip, and a second position where the end effector is prevented from fully forming a surgical clip.

In disclosed embodiments, the first jaw member defines a recess, and the second jaw member defines a recess. It is also disclosed that when the wedge is in the first position, the wedge is free from engagement with the recess of the first jaw member and with the recess of the second jaw member. It is further disclosed that when the wedge is in the second position, the wedge is engaged with the recess of the first jaw member and with the recess of the second jaw member.

BRIEF DESCRIPTION OF THE DRAWINGS

Embodiments of the disclosure are described in detail with reference to the drawing figures wherein like reference numerals identify similar or identical structural elements and.

DETAILED DESCRIPTION

Figure 1A:
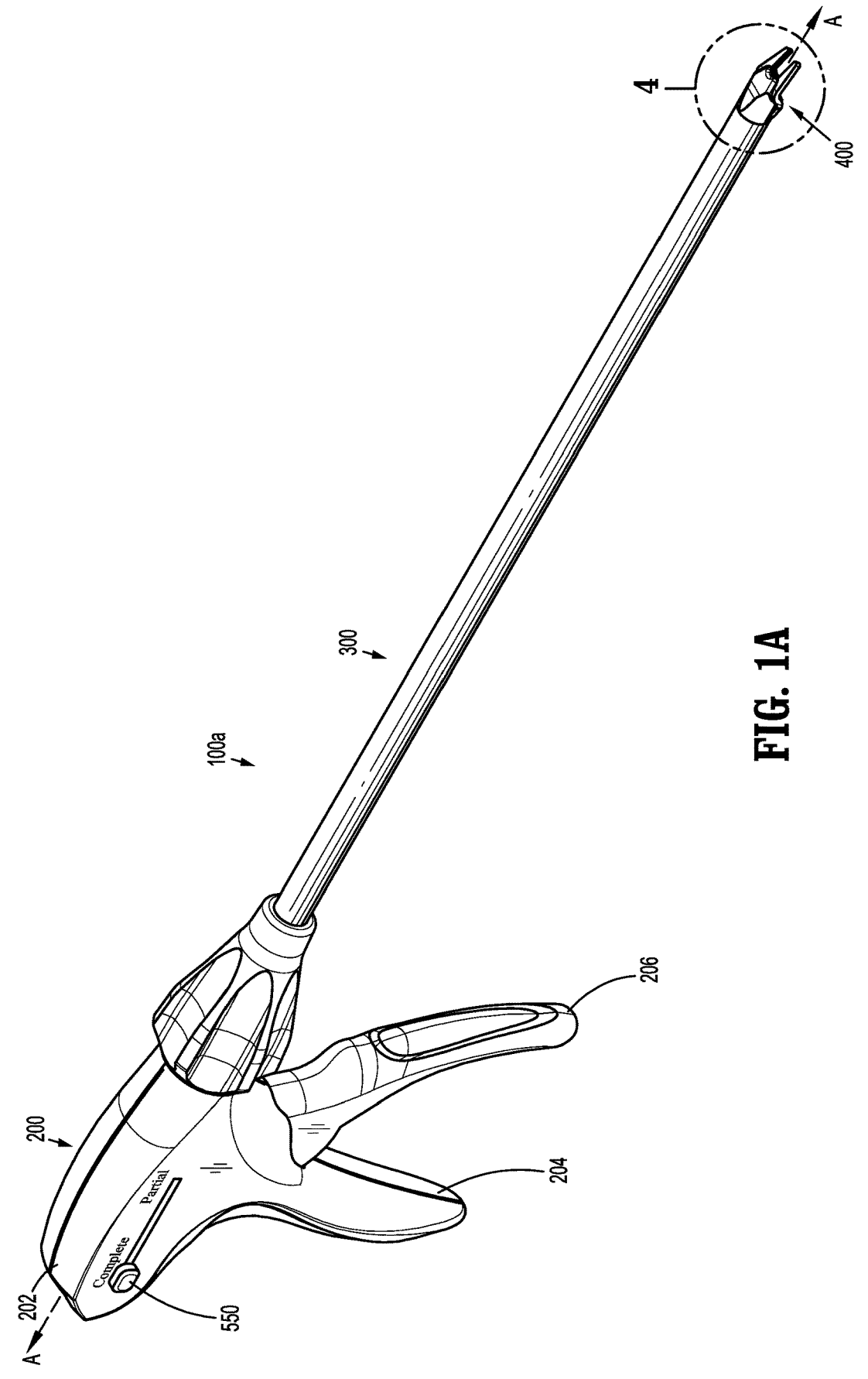
FIG. 1A is a front, perspective view of an endoscopic surgical clip applier illustrating a switch of a partial clip closure mechanism in a retracted position in accordance with embodiments of the disclosure.

Embodiments of the disclosed surgical clip applier are described in detail with reference to the drawings, in which like reference numerals designate identical or corresponding elements in each of the several views. Non-limiting examples of surgical clip appliers according to the disclosure include manual, robotic, mechanical and/or electromechanical, and the like. As used herein the term "distal" refers to that portion of the surgical clip applier, or component thereof, farther from the user, while the term "proximal" refers to that portion of the surgical clip applier, or component thereof, closer to the user.

As will be described in greater detail below, the disclosure includes a surgical clip applier having a partial clip closure mechanism that is selectively actuatable when it is desired to use the surgical clip applier to only partially form a clip. The partial clip closure mechanism, as well as related methods of use are also encompassed by this disclosure.

FIGS. 1A-21 illustrate surgical clip appliers in accordance with embodiments of the disclosure. More particularly, FIGS. 1A and 2-20 illustrate an endoscopic surgical clip applier 100A, FIG. 1B illustrates an open surgical clip applier 100B, and FIGS. 1C and 21 illustrate a robotic surgical clip applier 100C. While details of the endoscopic surgical clip applier 100A are discussed in detail herein, the disclosed partial clip closure mechanism 500 is also configured for use with the open surgical clip applier 100B and the robotic surgical clip applier 100C. For simplicity, each of the disclosed surgical clip appliers is generally referred to as surgical clip applier 100.

Figures 1B, 1C:
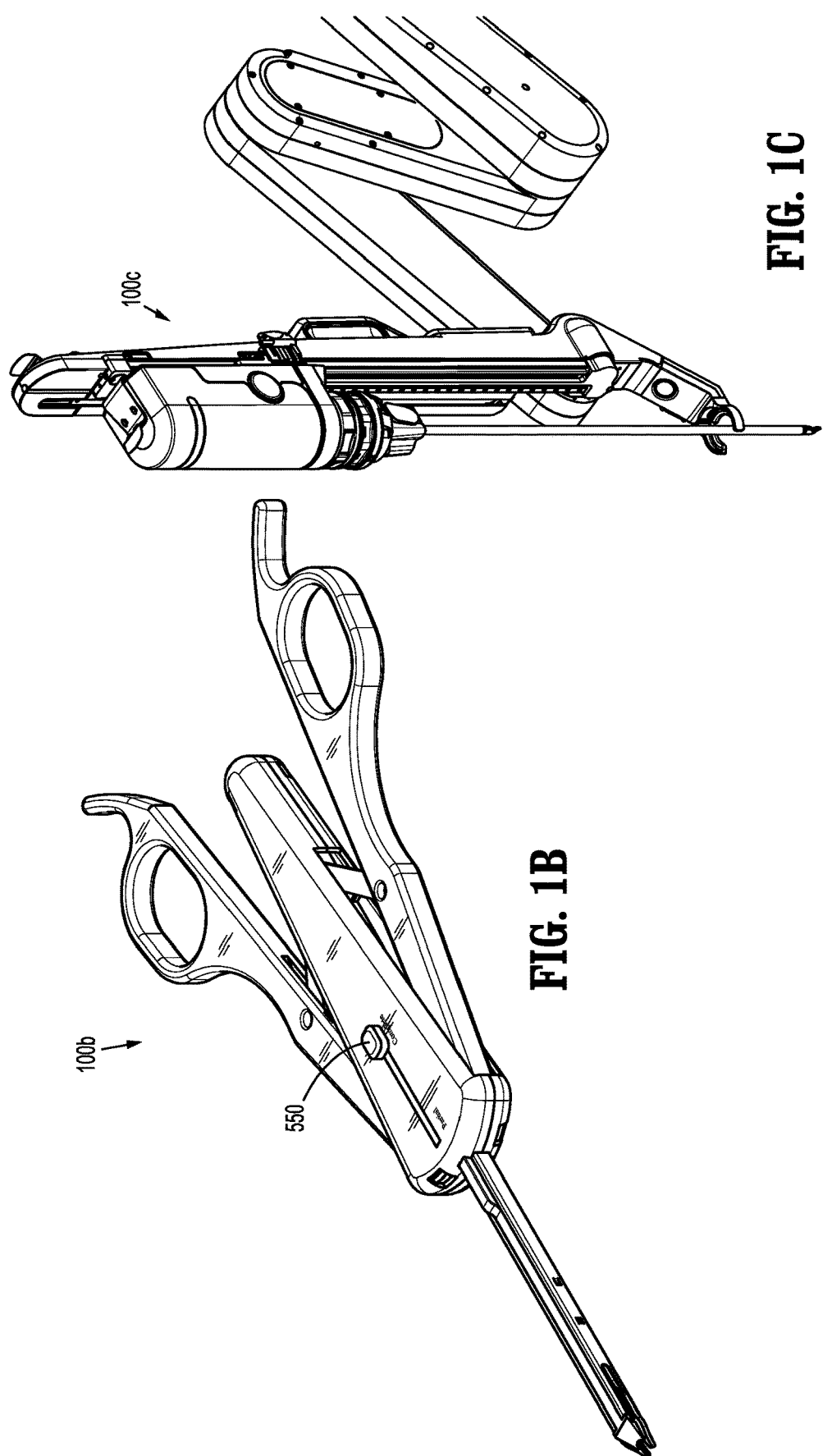
FIG. 1B is a front, perspective view of an open surgical clip applier in accordance with embodiments of the disclosure.
FIG. 1C is a front, perspective view of a robotic surgical clip applier in accordance with embodiments of the disclosure.
Figure 2:
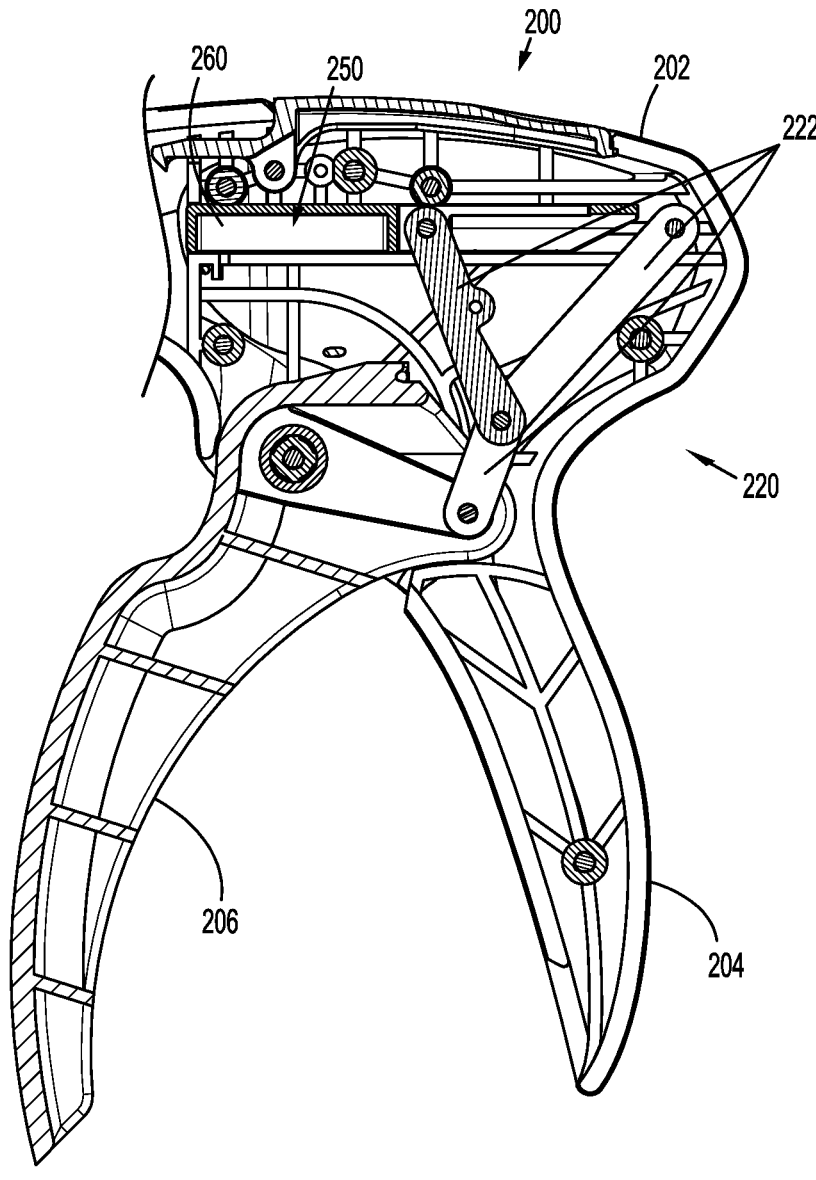
FIG. 2 is a side view of a handle assembly of the surgical clip applier of FIG. 1A, with portions removed, and illustrating a trigger of the surgical clip applier disposed in an un-actuated position.
Figure 3:
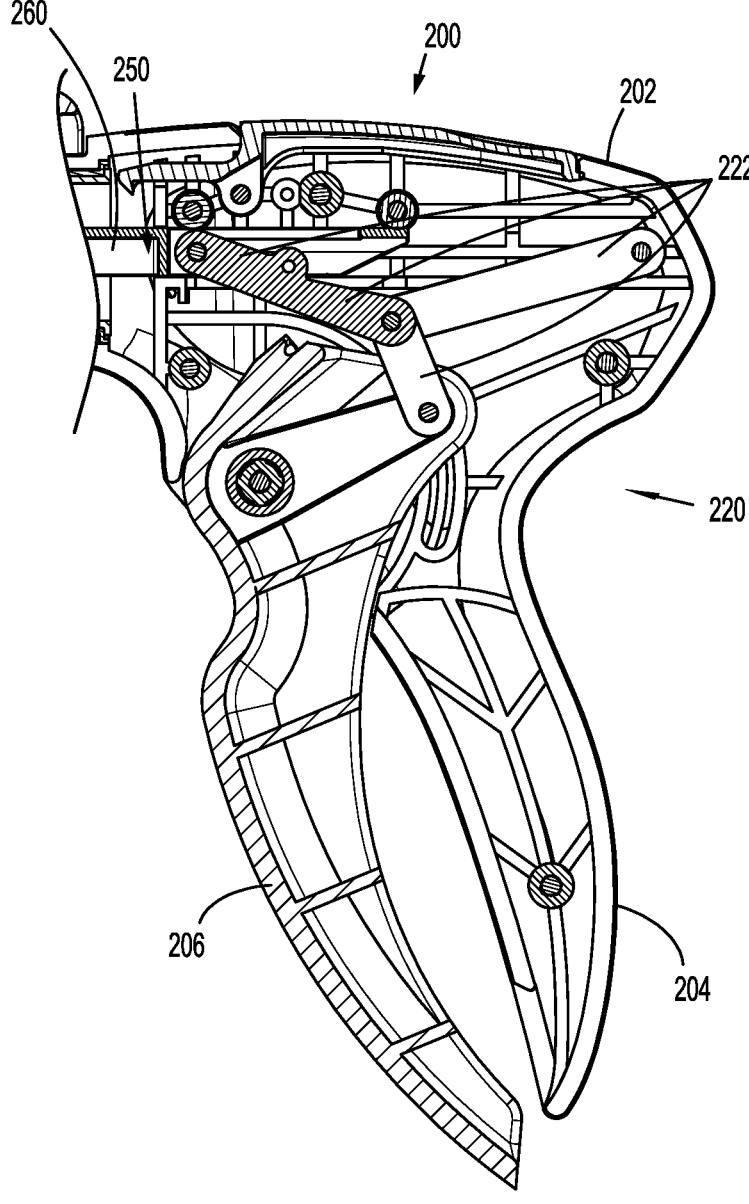
FIG. 3 is a side view of the handle assembly of the surgical clip applier of FIG. 1A, with portions removed, and illustrating the trigger in an actuated position.

With initial reference to FIG. 1A, the surgical clip applier 100 includes a handle assembly 200, an endoscopic or elongated portion 300 extending distally from the handle assembly 200 and defining a longitudinal axis "A-A," and an end effector (or pair of jaws) 400 disposed adjacent a distal end of the elongated portion 300. Additionally, an actuation assembly 220 (FIGS. 2-3) and a drive assembly 250 (FIGS. 2-3) are disposed in mechanical cooperation with the handle assembly 200 and are configured to distally advance and form surgical clips 600 (FIGS. 4-5).

While details of a particular handle assembly 200, a particular actuation assembly 220, and a particular drive assembly 250 are discussed below, the disclosed surgical clip applier 100 is usable with other types of handle assemblies, actuation assemblies, and drive assemblies without departing from the scope of the disclosure.

Figure 4:
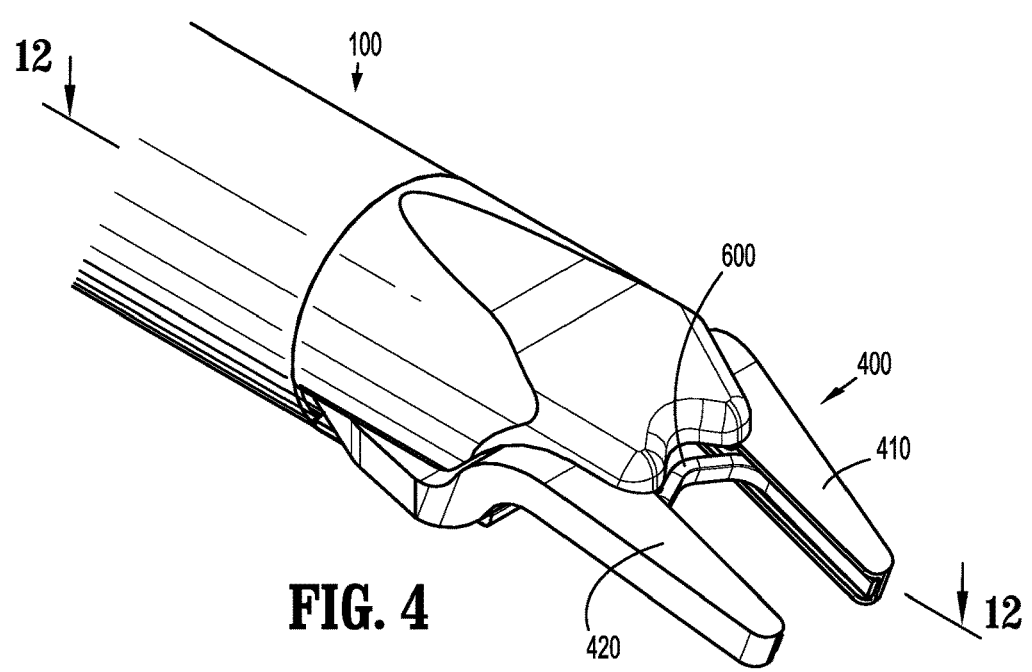
FIG. 4 is an enlarged view of the area of detail indicated in FIG. 1A illustrating a distal end of the surgical clip applier with a surgical clip therein.
Figure 5:
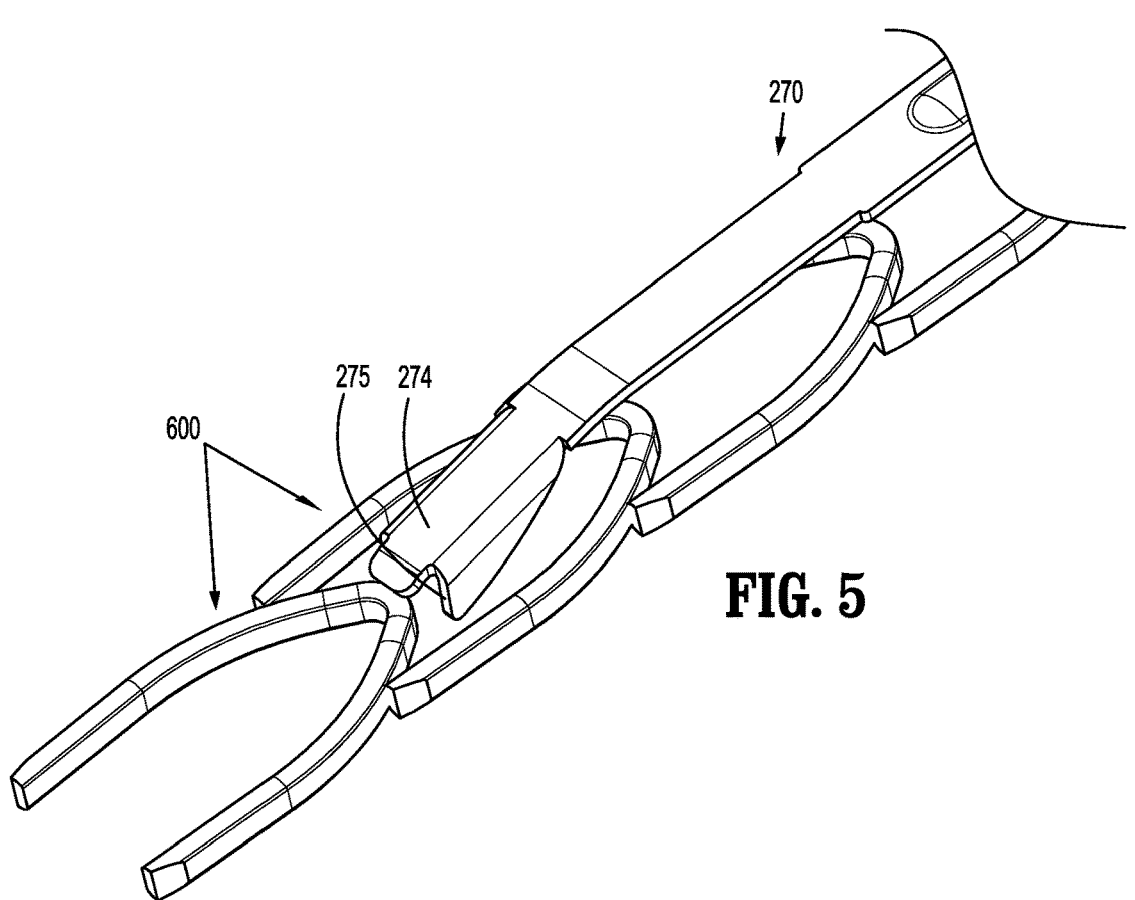
FIG. 5 is a perspective view of a distal portion of the surgical clip applier of FIG. 1A, with portions omitted, illustrating a plurality of surgical clips and a distal portion of a pusher assembly.
Figure 6:
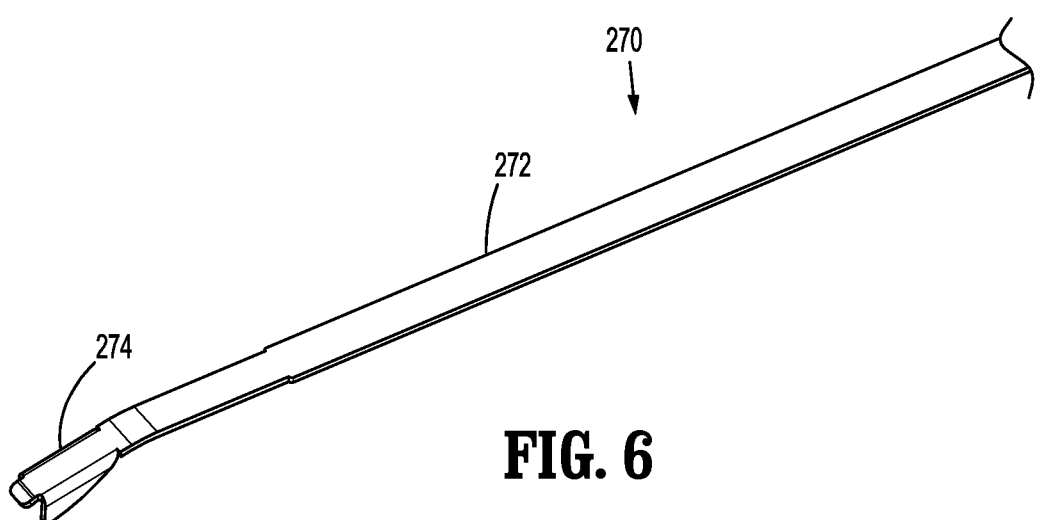
FIG. 6 is a perspective view of a portion of the pusher assembly of the surgical clip applier of FIG. 1A.

Referring now to FIGS. 2-7, further details of the handle assembly 200, the actuation assembly 220, the drive assembly 250, and the distal portion of the surgical clip applier 100 are shown. The handle assembly 200 includes a handle housing 202, a stationary handle 204, and a pivotable handle 206. The actuation assembly 220 includes a plurality of linkages 222 disposed in operative engagement with the pivotable handle 206. The drive assembly 250 includes a driver 260 and a pusher assembly 270 (FIGS. 5-6). Generally, actuation of the pivotable handle 206 causes at least portions of the drive assembly 250 to move distally, which in turn, causes formation and/or distal advancement of a surgical clip 600. Further details of suitable drive assemblies and actuation assemblies are described in U.S. patent application Ser. No. 17/572,669, filed on Jan. 11, 2022, and U.S. Pat. No. 11,246,601, filed on Jun. 6, 2019, the entire contents of each of which are incorporated by reference herein.

Figure 7:
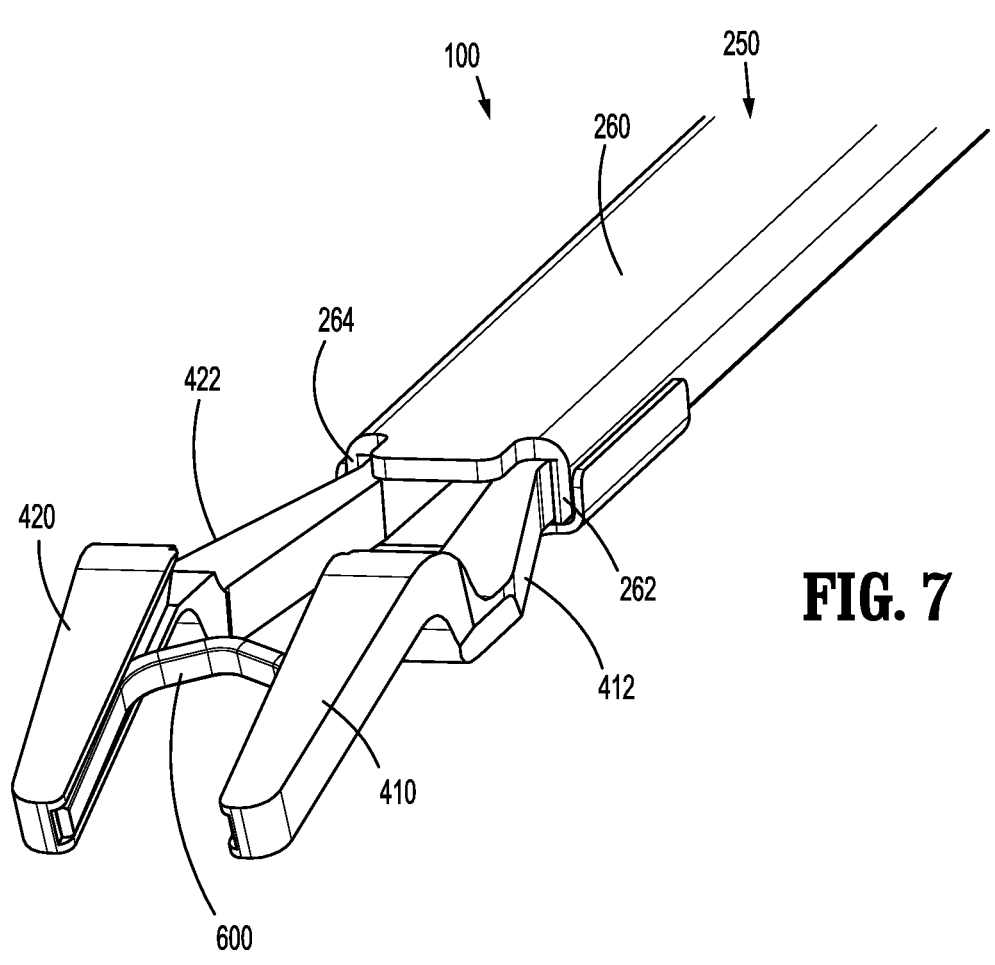
FIG. 7 is a perspective view of the distal portion of the surgical clip applier of FIG. 1A, with portions omitted, illustrating a surgical clip, jaw members, and a portion of a drive assembly.
Figure 8:
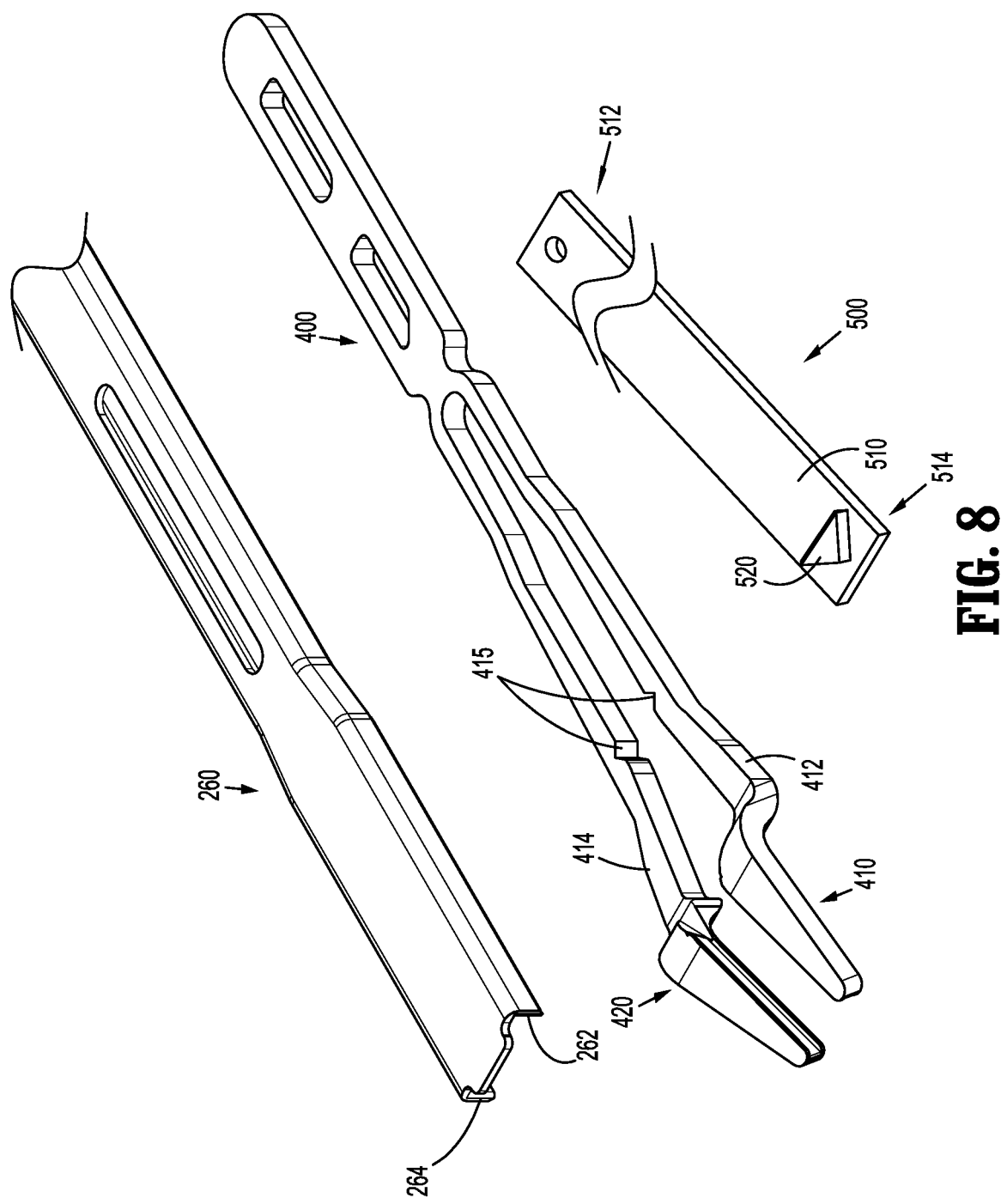
FIG. 8 is a perspective, exploded view of portions of the drive assembly, jaw members, and the partial clip closure mechanism of the surgical clip applier of FIG. 1A.

With particular reference to FIGS. 4, 5 and 7, the end effector 400 includes a first jaw member 410 and a second jaw member 420. The pusher assembly 270 advances surgical clips 600, one at a time, to a position between the first jaw member 410 and the second jaw member 420, and the driver 260 is advanced to move at least one of the first jaw member 410 or the second jaw member 420 toward the other and into a closed position, which compresses and forms the surgical clip 600 (e.g., through tissue). After the distal-most surgical clip 600 is formed (and ejected), subsequent actuation of the pivotable handle 206 results in distal advancement and formation of the next distal-most surgical clip 600. When the first jaw member 410 and the second jaw member 420 are in the closed position, the first jaw member 410 and the second jaw member 420 do not necessarily contact each other.

With particular reference to FIG. 6, portions of the pusher assembly 270 are shown. The pusher assembly 270 includes a pusher rod 272, and an engagement portion 274. The engagement portion 274 is disposed at a distal end of the pusher rod 274 and is configured to contact the distal-most surgical clip 600. As the pusher assembly 270 moves distally relative to the end effector 400, a pushing surface 275 of the pusher rod 274 engages the surgical clip 600 and moves the surgical clip 600 distally.

With specific reference to FIG. 7, distal movement of the driver 260 relative to the end effector 400, causes a first lateral surface 262 and a second lateral surface 264 of the driver 260 to engage ramped or camming surfaces 412, 422 of the first jaw member and the second jaw member, respectively. The engagement between the driver 260 and the camming surfaces 412, 422 of the respective first jaw member 410 and the second jaw member 420 as the driver 260 moves distally relative to the end effector 400 causes at least one of the first jaw member 410 or the second jaw member 420 to move into the closed position, thereby forming the surgical clip 600.

Figures 14, 15:
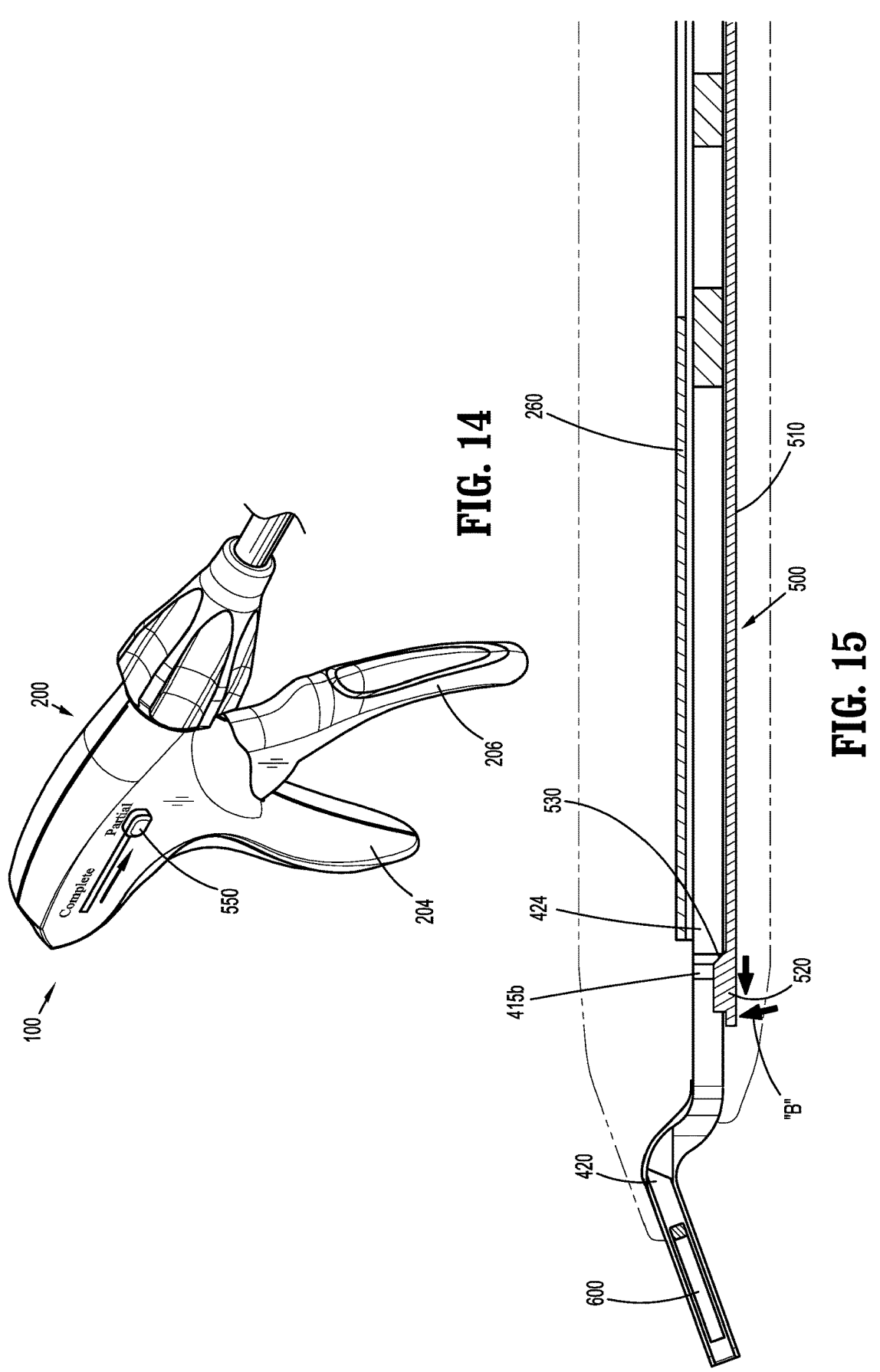
FIG. 14 is a perspective view of the handle assembly of the surgical clip applier of FIG. 1A illustrating the switch of the partial clip closure mechanism in an advanced position.
FIG. 15 is a cross-sectional view of the distal end of the surgical clip applier with a surgical clip therein illustrating the partial clip closure mechanism in the advanced position.
Figures 18, 19:
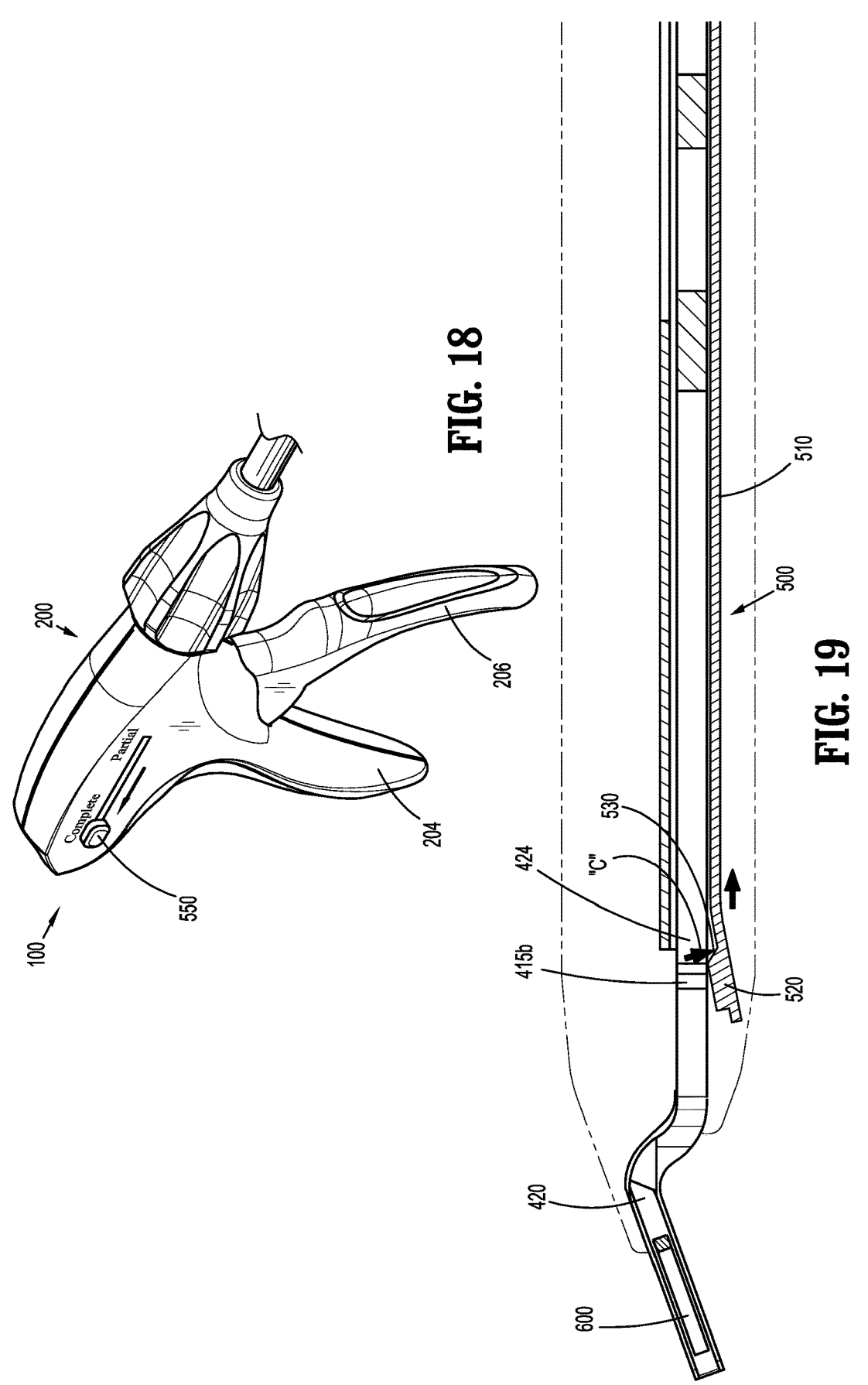
FIG. 18 is a perspective view of the handle assembly of the surgical clip applier of FIG. 1A illustrating the switch of the partial clip closure mechanism in the retracted position.
FIG. 19 is a cross-sectional view of the distal end of the surgical clip applier with a surgical clip therein illustrating the partial clip closure mechanism in a partially-retracted position.

Referring now to FIGS. 8-20, details of the partial clip closure mechanism 500 are shown. In general, and with particular reference to FIG. 8, the partial clip closure mechanism 500 includes an elongated link 510 and a wedge 520 extending/projecting from the elongated link 510, in a direction towards the first jaw member 410 and the second jaw member 420. A proximal portion 512 of the elongated link 510 is disposed in mechanical cooperation (e.g., coupled to) to a switch 550 on the housing 202 (FIGS. 1A, 14, and 18). The wedge 520 is disposed on a distal portion 514 of the elongated link 510 and is selectively engageable with recesses 415a, 415b (collectively, recesses 415) respectively defined by the first jaw member 410 and the second jaw member 420 of the end effector 400. As explained in further detail below, when the wedge 520 is engaged with the recesses 415a, 415b of the first and second jaw members 410, 420, the first and second jaw members 410, 420 are physically prevented from moving to the closed position, and are thereby unable to fully form the surgical fastener 600 supported by the first and second jaw members 410, 420.

Figures 9, 10, 11:
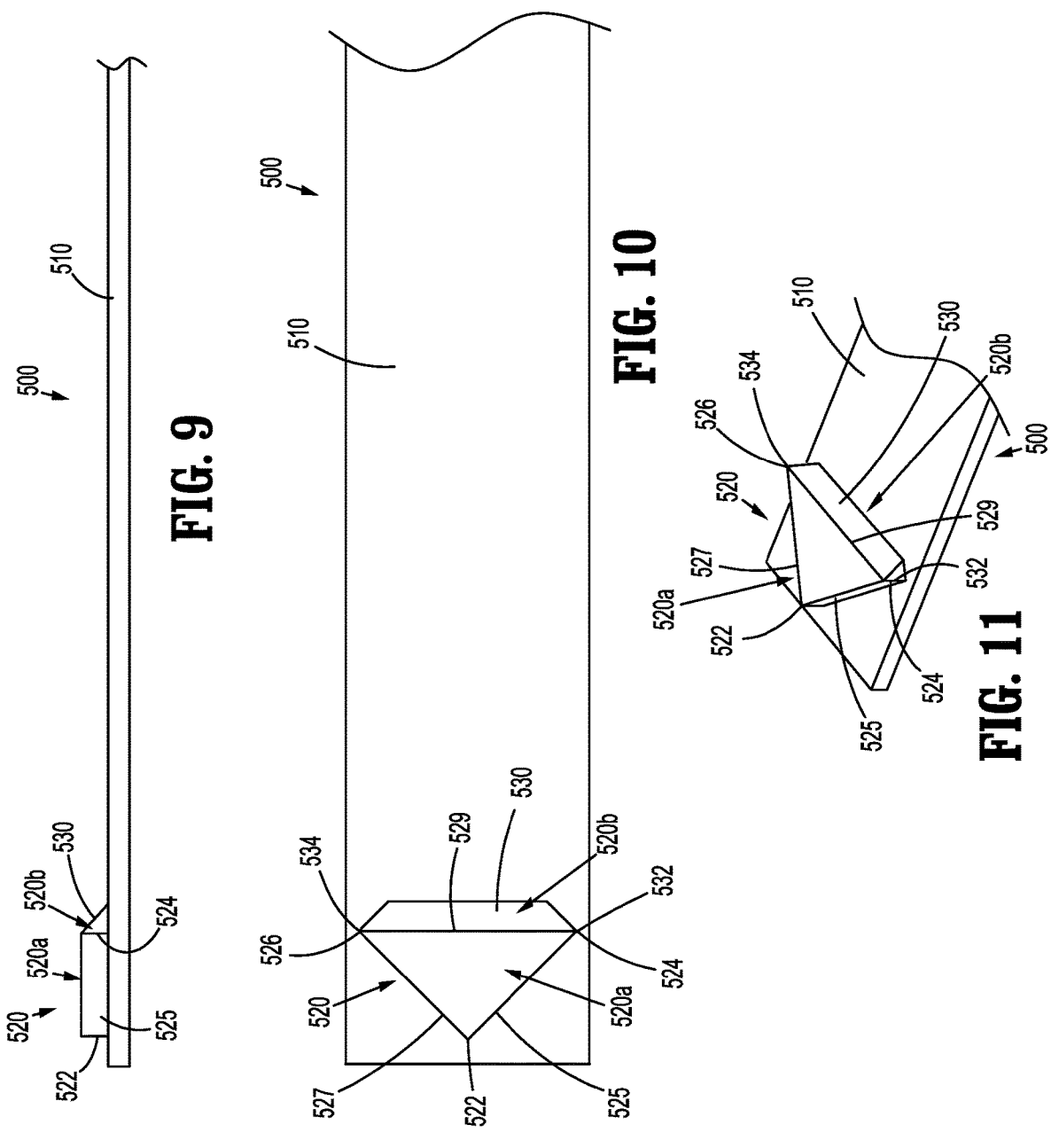
FIGS. 9 and 10 are side and plan views, respectively, of a portion of the partial clip closure mechanism of FIG. 8.
FIG. 11 is a perspective view of a distal portion of the partial clip closure mechanism of FIGS. 8-10.
Figure 12:
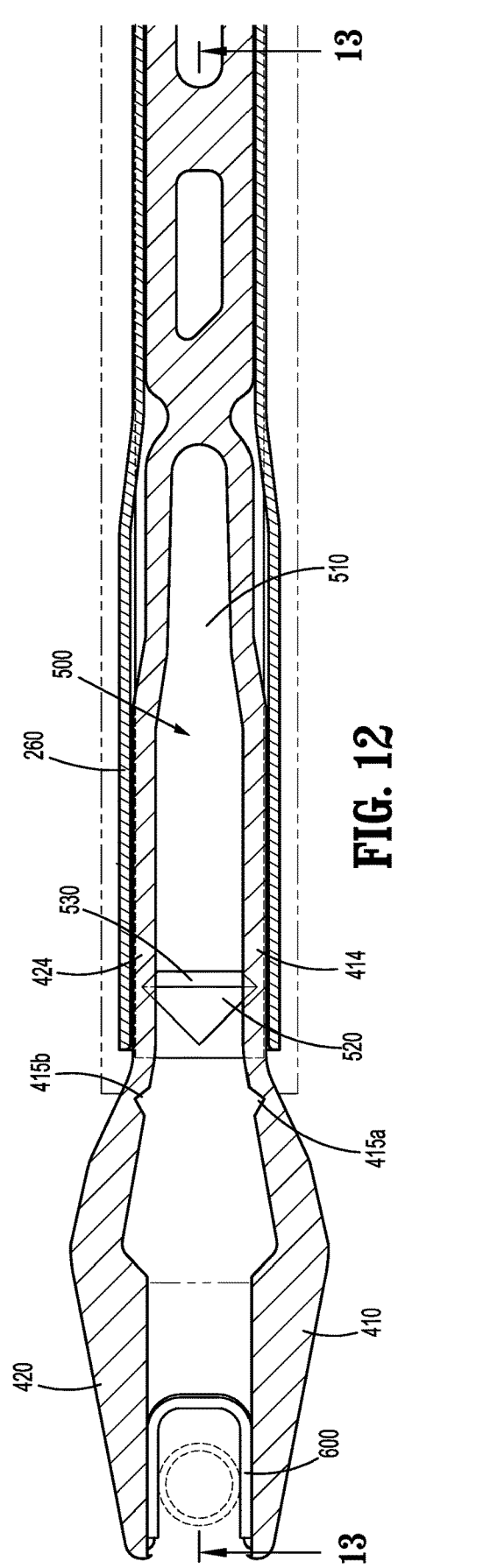
FIG. 12 is a cross-sectional view of the distal end of the surgical clip applier with a surgical clip therein taken along line 12-12 in FIG. 4 illustrating the partial clip closure mechanism in the retracted position.
Figure 13:
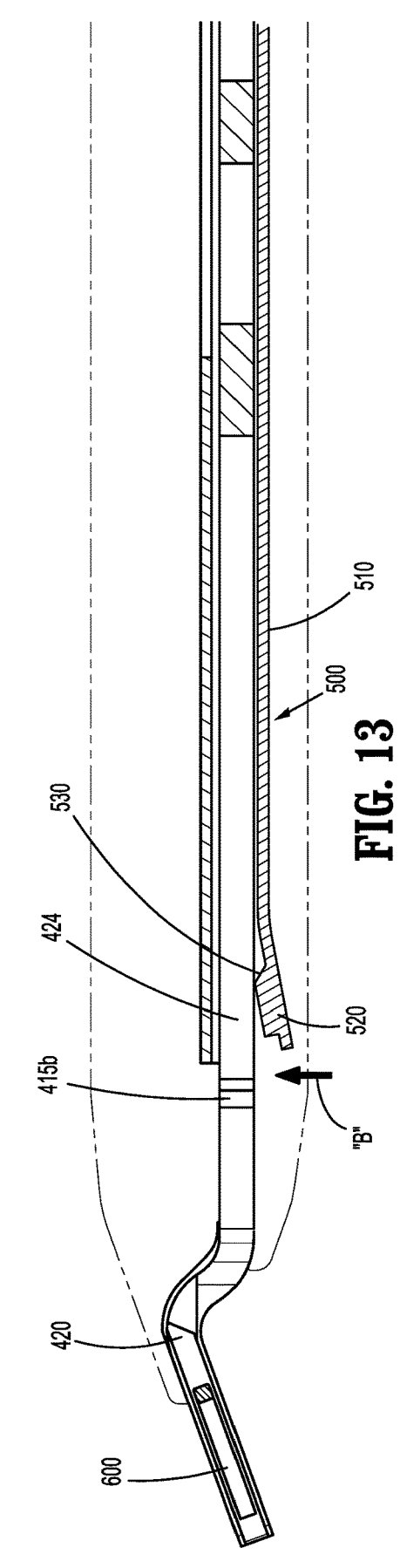
FIG. 13 is a cross-sectional view of the distal end of the surgical clip applier with a surgical clip therein taken along line 13-13 in FIG. 12 illustrating the partial clip closure mechanism in the retracted position.

With reference to FIGS. 9-11, further details of the wedge 520 of the partial clip closure mechanism 500 are shown. Generally, the wedge 520 defines a triangular portion 520a and a trapezoidal portion 520b (as viewed from above in FIG. 10). The triangular portion 520a of the wedge 520 includes a distal point 522, a first lateral point 524, a first lateral side 525 interconnecting the distal point 522 and the first lateral point 524, a second lateral point 526, a second lateral side 527 interconnecting the distal point 522 and the second lateral point 526, and a transverse side 529 interconnecting the first lateral point 524 and the second lateral point 526.

The trapezoidal portion 520b of the wedge 520 includes a ramp 530 and is disposed proximally of and in contact with the transverse side 529 of the triangular portion 520a of the wedge 520. The ramp 530 generally defines a trapezoid (as viewed from above in FIG. 10). In the illustrated embodiment, a first lateral point 532 of the ramp 530 contacts the first lateral point 524 of the triangular portion 520a of the wedge 520, and a second lateral point 534 of the ramp 530 contacts the second lateral point 526 of the triangular portion 520a of the wedge 520.

Figures 16, 17:
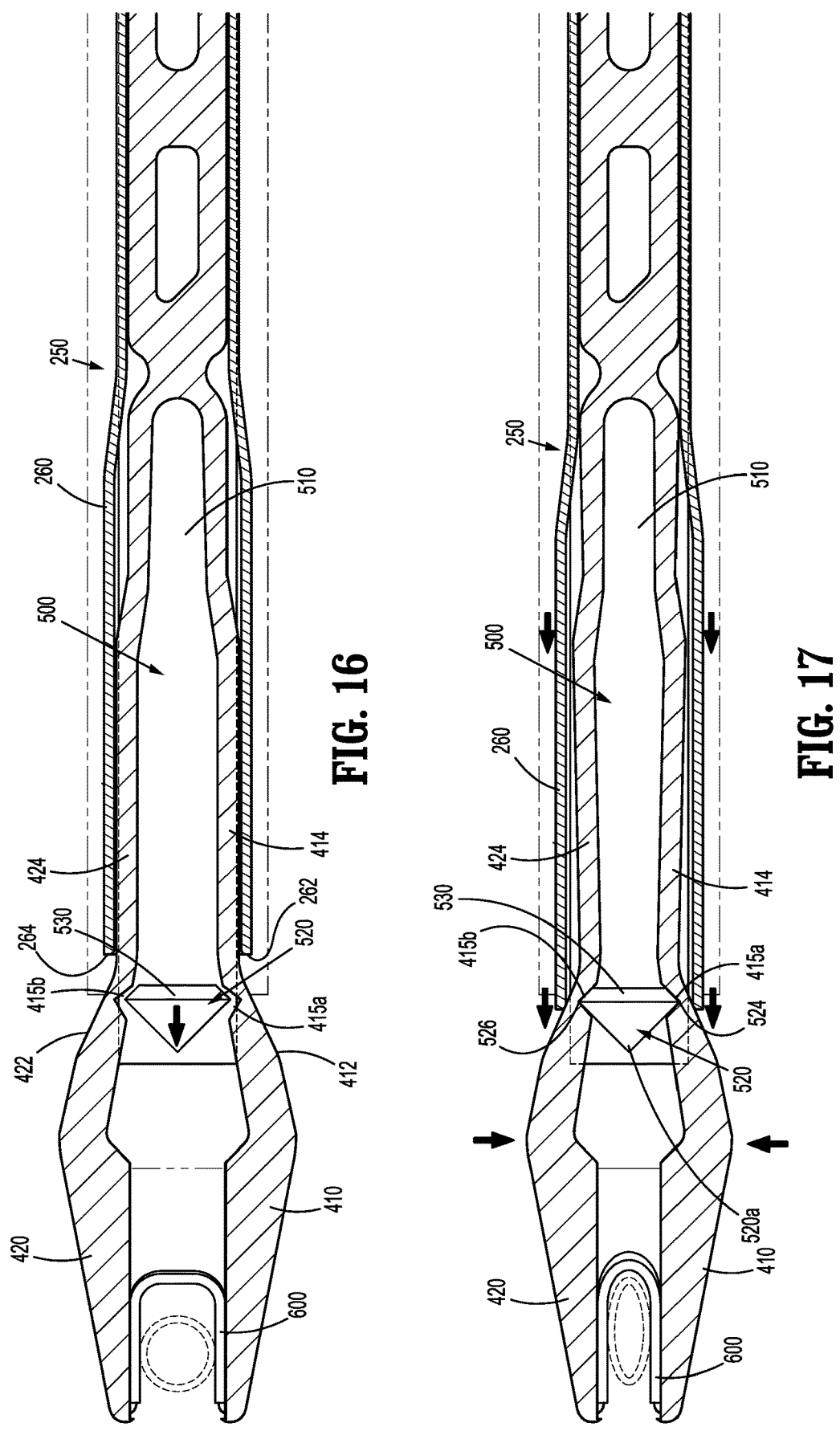
FIG. 16 is a cross-sectional view of the distal end of the surgical clip applier with an unformed surgical clip therein illustrating the partial clip closure mechanism in the advanced position and a portion of the drive assembly in a retracted position.
FIG. 17 is a cross-sectional view of the distal end of the surgical clip applier with a partially-formed surgical clip therein illustrating the partial clip closure mechanism in the advanced position and a portion of the drive assembly in an advanced position.

As shown in FIG. 17, when the wedge 520 is engaged with the recess 415a of the first jaw member 410 and the recess 415b of the second jaw member 420, at least the first lateral point 524 of the triangular portion 520a of the wedge 520 is at least partially within the first recess 415a, and at least the second lateral point 526 of the triangular portion 520a of the wedge 520 is at least partially within the second recess 415b. As shown in FIGS. 16 and 17, the shape of each recess 415a, 415b is complimentary to the shape of the portion of the wedge 520 that is configured to engage that recess 415a, 415b. In the illustrated embodiment, the recesses 415a, 415b are generally triangular.

In use, when a user desires to partially close a surgical clip 600 (e.g., to variably occlude a vessel, or to retain a catheter in a vessel without occluding the vessel such as during cholangiograms), the user advances the partial clip closure mechanism 500 by sliding the switch 550 distally (or ensures the switch 550 is already in its distal position). (Other structures for actuating or deploying the partial clip closure mechanism 500, such as depressing a button, are also envisioned.) Actuation of the partial clip closure mechanism 500 causes the elongated link 510 and the wedge 520 to move distally relative to the end effector 400, and causes the wedge 520 to move distally along rails 414, 424 of the first jaw member 410 and the second jaw member 420, respectively (see FIGS. 12 and 13). After sufficient distal translation of the wedge 520 relative to the end effector 400, portions of the wedge 520 of clip closure mechanism 500 become engaged with the recesses 415a, 415b defined by the first jaw member 410 and the second jaw member 420, respectively, thereby limiting the amount of movement the jaw members 410, 420 can move toward each other. Additionally, in embodiments, the distal portion 514 of the elongated link 510 (e.g., the portion of the elongated link 510 including the wedge 520) is biased in the general direction of arrow "B" in FIG. 13, thereby facilitating engagement between the wedge 520 and the recesses 415 of the jaw members 410, 420.

With reference to FIGS. 15-17, when the partial clip closure mechanism 500 is in the distal position, actuation of the drive assembly 250 (e.g., by pivoting the pivotable handle 206) distally advances a surgical clip 600 between the jaw members 410, 420, and advances the driver 260 of the drive assembly 250 to partially close the first jaw member 410 and the second jaw member 420, which compresses and partially forms the surgical clip 600. That is, as discussed above with regard to FIG. 7, distal movement of the driver 260 causes the first lateral surface 262 and the second lateral surface 264 of the driver 260 to engage the camming surfaces 412, 422 of the first jaw member 410 and the second jaw member 420, respectively, which causes at least a partial closure of the first jaw member 410 and the second jaw member 420, thereby at least partially forming the surgical clip 600. Here, in FIGS. 15-17, since the wedge 520 is engaged with the recesses 415a, 415b, the jaw members 410, 420 are prevented from fully closing, and the surgical clip 600 is only able to be partially formed.

Figure 20:
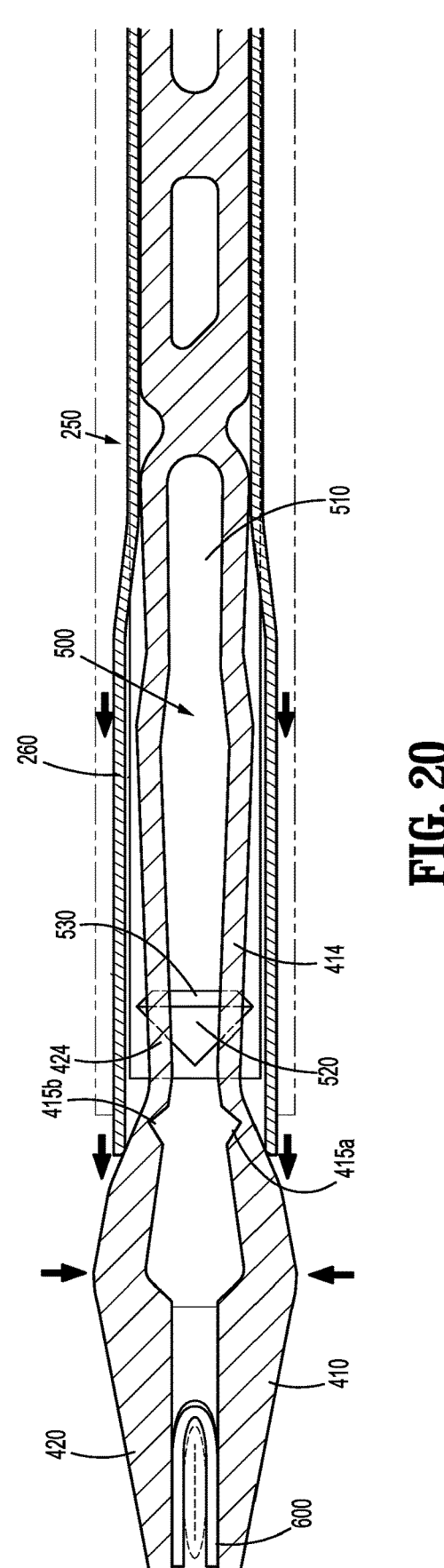
FIG. 20 is a cross-sectional view of the distal end of the surgical clip applier with a fully-formed surgical clip therein illustrating the partial clip closure mechanism in the retracted position and a portion of the drive assembly in an advanced position.
Figure 21:
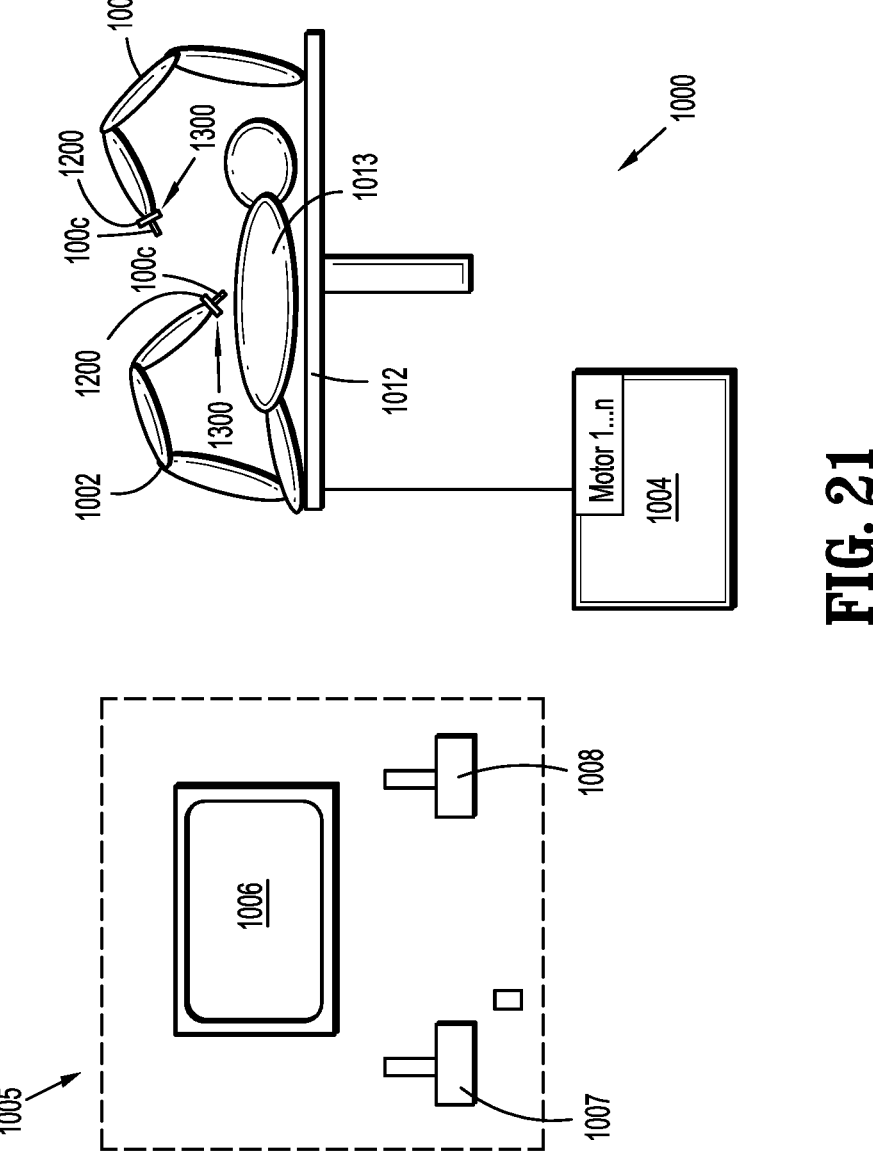
FIG. 21 is a schematic illustration of a robotic surgical system configured for use in accordance with the disclosure.

With reference to FIGS. 18-20, when a user desires to fully close a surgical clip 600, the user retracts the partial clip closure mechanism 500 by sliding the switch 550 proximally (or ensures the switch 550 is already in its proximal position; FIG. 18). Initially, retraction of the partial clip closure mechanism 500 causes the wedge 520 to disengage from the recesses 415a, 415b of the first and second jaw members 410, 420, respectively, by moving in the general direction of arrow "C" in FIG. 19. The ramp 530 of the wedge 520 facilitates disengagement between the wedge 520 and the recesses 415a, 415b of the jaw members 410, 420, respectively, when the wedge 520 is moved proximally relative to the end effector 400. Continued proximal movement of the switch 550 causes the elongated link 510 and the wedge 520 to move proximally relative to the end effector 400, and along the rails 414, 424 of the first jaw member 410 and the second jaw member 420, respectively (see FIG. 19). After sufficient proximal translation of the wedge 520 relative to the end effector 400, the partial clip closure mechanism 500 is in its proximal position (FIG. 20).

With reference to FIG. 20, when the partial clip closure mechanism 500 is in the proximal position, actuation of the drive assembly 250 (e.g., by pivoting the pivotable handle 206) distally advances a surgical clip 600 between the jaw members 410, 420, and advances the driver 260 of the drive assembly 250 to move at least one of the first jaw member 410 or the second jaw member 420 toward the other and into a closed position, which compresses and fully forms the surgical clip 600. Here, the wedge 520 does not restrict the amount of closure of the jaw members 410, 420, thereby allowing a surgical clip 600 to be fully formed As described, the partial clip closure mechanism 500 functions independently of the drive assembly 250. Accordingly, prior to (or during) the deployment of each surgical clip 600, the user has the option to fully- or partially-form the surgical clip 600 by positioning the partial clip closure mechanism 500 in the proximal position (e.g., FIGS. 12, 13 and 20) or in the distal position (e.g., FIGS. 15-17), respectively.

The various embodiments disclosed herein may also be configured to work with robotic surgical systems and what is commonly referred to as "Telesurgery." Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

With reference to FIG. 21, a surgical system, such as, for example, a robotic surgical system is shown generally as surgical system 1000 and is usable with the surgical clip applier 100c, or portions thereof, of the disclosure. Surgical system 1000 generally includes a plurality of robotic arms 1002, 1003, a control device 1004, and an operating console 1005 coupled with control device 1004. Operating console 1005 includes a display device 1006, which is set up in particular to display three-dimensional images; and manual input devices 1007, 1008, by means of which a person (not shown), for example a surgeon, is able to telemanipulate robotic arms 1002, 1003 in a first operating mode, as known in principle to a person skilled in the art.

Each of the robotic arms 1002, 1003 is composed of a plurality of members, which are connected through joints. System 1000 also includes an instrument drive unit 1200 connected to distal ends of each of robotic arms 1002, 1003. The surgical clip applier 100c may be attached to the instrument drive unit 1200, in accordance with any one of several embodiments disclosed herein, as will be described in greater detail below.

Robotic arms 1002, 1003 may be driven by electric drives (not shown) that are connected to control device 1004. Control device 1004 (e.g., a computer) is set up to activate the drives, in particular by means of a computer program, in such a way that robotic arms 1002, 1003, their instrument drive units 1200 and thus the surgical instrument 10 (including end-effector assembly 22) execute a desired movement according to a movement defined by means of manual input devices 1007, 1008. Control device 1004 may also be set up in such a way that it regulates the movement of robotic arms 1002, 1003 and/or of the drives.

Surgical system 1000 is configured for use on a patient 1013 lying on a patient table 1012 to be treated in a minimally invasive manner by means of the surgical clip applier 100c. Surgical system 1000 may also include more than two robotic arms 1002, 1003, the additional robotic arms likewise being connected to control device 1004 and being telemanipulatable by means of operating console 1005.

Reference may be made to U.S. Patent Publication No. 2012/0116416, filed on Nov. 3, 2011, now U.S. Pat. No. 8,828,023, entitled "Medical Workstation," the entire content of which is incorporated herein by reference, for a detailed discussion of the construction and operation of surgical system 1000.

It should be understood that the foregoing description is only illustrative of the disclosure. Various alternatives and modifications can be devised by those skilled in the art without departing from the disclosure. Accordingly, this disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical clip applier, comprising:

an elongated portion including a distal end;

an end effector disposed adjacent the distal end of the elongated portion, the end effector including a first jaw member and a second jaw member, the first jaw member defining a first recess, the end effector configured to support a surgical clip between the first jaw member and the second jaw member;

a partial clip closure mechanism comprising an elongated link having a distal portion, and a wedge a projecting from the distal portion of the elongated link, the wedge having a trapezoidal portion defined by a ramp and a triangular portion defined by at least a first lateral corner, the first lateral corner and a first side of the ramp forming a first edge dimensioned to be received into a first shape of the first recess; and a driver, wherein distal advancement of the driver along the elongated portion urges the first jaw member toward the second jaw member from an open position to a closed position, wherein distal advancement of the elongated link biases the first edge of the wedge into engagement with at least the first recess of the first jaw member, positioning the first jaw member and the second jaw member in a partially closed position.

2. The surgical clip applier according to claim 1, wherein when the first jaw member and the second jaw member are positioned in the partially closed position, the surgical clip is partially formed between the first jaw member and the second jaw member.

3. The surgical clip applier according to claim 1, wherein the second jaw member defines a second recess, wherein a distal side of the wedge is further defined by at least a second lateral corner, the second lateral corner and a second side of the ramp forming a second edge dimensioned to be received into a second shape of the second recess, and wherein the distal advancement of the elongated link biases the second edge of the wedge into engagement with the second recess of the second jaw member.

4. The surgical clip applier according to claim 1, wherein the ramp facilitates disengagement between the first edge of the wedge and at least the first recess of the first jaw member.

5. The surgical clip applier according to claim 1, wherein the first jaw member includes a first rail, and the second jaw member includes a second rail, and wherein the wedge is longitudinally translatable along the first rail of the first jaw member and along the second rail of the second jaw member.

6. The surgical clip applier according to claim 1, wherein the partial clip closure mechanism includes a switch disposed in mechanical cooperation with a proximal portion of the elongated link, and wherein activation of the switch advances the distal portion of the elongated link to bias the first edge of the wedge into engagement with at least the first recess of the first jaw member.

7. The surgical clip applier according to claim 1, wherein selective retraction of the elongated link disengages the first edge of the wedge from at least the first recess of the first jaw member, enabling the first jaw member and the second jaw member to be urged into the closed position by the driver.

8. The surgical clip applier according to claim 7, wherein when the first jaw member and the second jaw member are positioned in the closed position, the surgical clip is fully formed between the first jaw member and the second jaw member.

9. The surgical clip applier of claim 1, wherein the wedge projects laterally relative to a longitudinal axis of the elongated link.

10. A surgical clip applier, comprising:

an elongated portion defining a longitudinal axis and including a distal end;

an end effector disposed adjacent the distal end of the elongated portion, the end effector including a first jaw member and a second jaw member, the first jaw member defining a recess, wherein the end effector is configured to support a surgical clip between the first jaw member and the second jaw member;

a driver, wherein distal advancement of the driver along the elongated portion urges the first jaw member toward the second jaw member from an open position to a closed position; and a partial clip closure mechanism comprising an elongated link and a wedge projecting from the elongated link, the wedge having a trapezoidal portion defined by a ramp and a triangular portion defined by at least a lateral corner, the lateral corner and a first side of the ramp forming an edge of the wedge dimensioned to be received into a complementary shape of the recess, wherein selective movement of the elongated link biases the edge of the wedge between:

engagement with at least the recess of the first jaw member to cause the first jaw member to be positioned in a partially closed position relative to the second jaw member, and disengagement with at least the recess of the first jaw member to allow the first jaw member to be positioned in the closed position relative to the second jaw member.

11. The surgical clip applier according to claim 10, wherein the wedge is movable in a direction that is parallel to the longitudinal axis.

12. The surgical clip applier according to claim 11, wherein the wedge is movable in a direction that is disposed at an angle to the longitudinal axis.

13. The surgical clip applier according to claim 10, wherein the ramp facilitates proximal movement of the edge of the wedge to disengage at least the recess of the first jaw member.

14. The surgical clip applier according to claim 10, wherein the first jaw member includes a first rail, and the second jaw member includes a second rail, and wherein the wedge is longitudinally translatable along the first rail of the first jaw member and along the second rail of the second jaw member.

15. The surgical clip applier according to claim 10, wherein the selective movement of the elongated link is selective retraction to bias the edge of the wedge into disengagement from at least the first recess of the first jaw member.

16. The surgical clip applier according to claim 10, wherein the selective movement of the elongated link is selective advancement to bias the edge of the wedge into engagement with at least the first recess of the first jaw member.

17. The surgical clip applier of claim 10, wherein the wedge projects laterally relative to the longitudinal axis.

18. A surgical clip applier, comprising:

an elongated portion including a distal end;

an end effector disposed adjacent the distal end of the elongated portion, the end effector including a first jaw member having a first recess and a second jaw member having a second recess, the end effector configured to support a surgical clip between the first jaw member and the second jaw member;

a driver, wherein distal advancement of the driver along the elongated portion urges at least the first jaw member from an open position to a closed position with respect to the second jaw member; and a partial clip closure mechanism comprising an elongated link and a wedge projecting from the elongated link, the wedge having a trapezoidal portion defined by a ramp and a triangular portion defined by at least a first lateral corner, the first lateral corner and a first side of the ramp forming a first edge dimensioned to be received into a first shape of the first recess, wherein selective movement of the elongated link biases the wedge between:

a first position in which the first edge of the wedge is disengaged with at least the first recess of the first jaw member, enabling the end effector to fully form a surgical clip, and a second position in which the first edge of the wedge is engaged with at least the first recess of the first jaw member, enabling the end effector to partially form a surgical clip.

19. The surgical clip applier according to claim 18, a distal side of the wedge having at least a second lateral corner, the second lateral corner and a second side of the ramp forming a second edge dimensioned to be received into a second shape of the second recess, wherein when the wedge is in the first position, the second edge of the wedge is disengaged with the second recess of the second jaw member.

20. The surgical clip applier according to claim 19, wherein when the wedge is in the second position, the second edge of the wedge is engaged with the second recess of the second jaw member.

\* \* \* \* \*